United States Patent [19]

Daniels et al.

[11] Patent Number: 4,828,630
[45] Date of Patent: May 9, 1989

[54] DUPLEX STAINLESS STEEL WITH HIGH MANGANESE

[75] Inventors: James A. Daniels, Loveland; Joseph A. Douthett, Monroe; John G. Tack, Middletown, all of Ohio

[73] Assignee: Armco Advanced Materials Corporation, Lyndora, Pa.

[21] Appl. No.: 152,178

[22] Filed: Feb. 4, 1988

[51] Int. Cl.$^4$ .............................................. C22C 38/58
[52] U.S. Cl. .................................. 148/325; 148/327; 420/56; 420/57; 420/61; 75/246
[58] Field of Search ................... 148/325, 327; 420/33, 420/56-58, 60, 61, 67; 75/246

[56] References Cited

U.S. PATENT DOCUMENTS

| | | | |
|---|---|---|---|
| 3,567,434 | 3/1971 | Richardson et al. | 75/125 |
| 3,736,131 | 5/1973 | Espy | 74/126 B |
| 3,861,908 | 1/1975 | Bressanelli | 75/126 B |
| 3,865,644 | 2/1975 | Hellner et al. | 148/37 |
| 3,926,685 | 12/1975 | Geussier et al. | 148/12 EA |
| 3,929,520 | 12/1975 | Hellner et al. | 148/37 |
| 4,101,347 | 7/1978 | Fujikura et al. | 148/38 |
| 4,657,606 | 4/1987 | Guha | 148/327 |
| 4,659,397 | 4/1987 | Kobayashi et al. | 148/12 E |
| 4,664,725 | 5/1987 | Fujiwara et al. | 148/325 |
| 4,715,908 | 12/1989 | Churchill | 148/327 |

FOREIGN PATENT DOCUMENTS 156778 10/1985 European Pat. Off. .
181257 9/1985 Japan .

Primary Examiner—Deborah Yee
Attorney, Agent, or Firm—Larry A. Fillnow; Robert J. Bunyard; Robert H. Johnson

[57] ABSTRACT

A duplex stainless steel which is economical and balanced to provide a good combination of properties in the as-cast condition and resists thermal transformation to martensite due the high levels of manganese. This steel is particularly suited for thin-walled castings for automotive underbody components. It is 30% to 60% ferrite and balance austenite and, in weight percent, consists essentially of:

C - up to 0.07,
Cr - 17 to 21.5,
Ni - greater than 1 to less than 4,
Mn - greater than 4 to 8,
N - 0.05 to 0.15,
Si - less than 2,
Mo - less than 2,
Cu - less than 1.5 and balance essentially Fe.

13 Claims, No Drawings

DUPLEX STAINLESS STEEL WITH HIGH MANGANESE

TECHNICAL FIELD

The present invention relates to duplex stainless steels and particularly to duplex stainless steels having excellent as-cast properties, including good ductility, corrosion resistance, toughness and strength. These as-cast properties are obtainable without a heat treatment.

The duplex stainless steels of the present invention are thermally stable against transformation to martensite.

Thin-walled castings for automotive underbody components, such as spindle links and exhaust manifolds, are easily cast from the composition and have excellent properties as-cast. The duplex stainless steel may also be produced in other forms such as castings, strip, sheet, bar, rod and wire.

BACKGROUND ART

U.S. Pat. No. 3,567,434 is one of the earlier attempts to use high levels of nitrogen in a high chromium duplex stainless steel. The steels have manganese contents below 3%.

Japanese Publication No. 60-181257 discloses a high manganese content (3% to 10%) in a duplex stainless steel having high silicon.

U.S. Pat. No. 4,101,347 includes 0.08% to 0.25% nitrogen in a high chromium duplex stainless steel to stabilize the austenite and improve corrosion resistance. Manganese must be restricted to levels below 2% to avoid sigma phase.

U.S. Pat. No. 4,657,606 adds 5% to 7% manganese to a high chromium duplex stainless steel to simplify the cooling after solution heat treatment. The duplex alloy as 1.1% to 3% copper in the steel composition.

U.S. Pat. No. 4,664,725 has up to 4% manganese added to a duplex stainless steel to stabilize the austenite and provide solubility for nitrogen which can be from 0.06% to 0.20%. At least 2% molybdenum is essential in this steel.

DISCLOSURE OF THE INVENTION

A duplex stainless steel as-cast having 30% to 60% ferrite and remainder austenite has a composition balanced for optimum as-cast strength, ductility, toughness and corrosion resistance. The composition is also balanced to provide these properties with less expensive alloying elements than prior alloys. The composition may be used in various wrought forms.

The composition of the duplex stainless steel consists essentially of, in weight percent, carbon below 0.07% and preferably below 0.04%, chromium from 17% to 21.5% and preferably 18.5% to 20%, nickel from above 1% to less than 4% and preferably 2% to 3%, manganese from greater than 4% to 8% and preferably from 4.25% to 5.5%, nitrogen from 0.05% to 0.15% and preferably 0.07% to 0.13%, silicon less than 2% and preferably less than 1.3%, molybdenum less than 2% and preferably less than 1.25%, copper less than 1.5% and preferably less than 1% and balance essentially iron.

A duplex stainless steel article produced from this composition will have as-cast properties including a 10% minimum elongation (1 inch/2.5 cm) a 0.2% yield strength greater than 50 ksi (350 N/mm$^2$), a toughness of at least 20 ft.-lbs. (30 Nm) at 32° F.(0° C.), and no nitrogen porosity.

It is a principal object of our invention to provide a duplex stainless steel composition which has improved resistance to sigma phase and 885° F. (475° C.) embrittlement.

It is a further object of our invention to reduce the expensive alloying elements, particularly chromium, molybdenum and nickel.

Another object of the invention is to provide a composition which may be used in the cast form which does not require solution treatment or delicate control of the cooling rates.

A still further object of our invention is to provide a composition balance which provides good strength, corrosion resistance, ductility and toughness while being alloyed to prevent thermal transformation to martensite.

BEST MODE FOR CARRYING OUT THE INVENTION

Duplex stainless steels which are 30% to 60% ferrite and balance austenite have found extensive use for resisting intercrystalline corrosion and pitting while providing high levels of strength. These properties are provided by high levels of chromium and molybdenum and a balancing proportion of nickel. Using various relationships for chromium equivalents and nickel equivalents, other elements are included in the balance between austenite and ferrite.

A duplex stainless steel or article of the present invention has the following composition:
less than 0.07% C,
17% to 21.5% Cr,
greater than 1% to less than 4% Ni,
0.05% to 0.15% N,
greater than 4% to 8% Mn,
less than 2% Si,
less than 2% Mo,
less than 1.5% Cu,
up to 1% Nb, Ti, Ta, Zr and/or V,
up to 0.01% Ca,
up to 0.10% P,
up to 0.4% S,
up to 0.2% Ce,
up to 0.01% B, and balance essentially Fe, Carbon is maintained below 0.07% in the duplex alloy to control carbide precipitation which hurts intergranular corrosion and reduces ductility and toughness. Preferably, the carbon is restricted to a level below 0.04%. The carbon present does provide some strength during casting and is an austenite former.

Chromium is lowered from conventional duplex levels to 17% to 21.5%. This level of chromium still provides good corrosion resistance but reduces the solubility of nitrogen in the alloy. A preferred chromium range is 18.5% to 20%. Chromium is a strong ferrite former which contributes to sigma phase and 885° F.(475° C.) embrittlement. By lowering the chromium content, the nickel content also may be lowered and the same austeniteferrite balance maintained.

Nickel is reduced from a typical range of 4% to 7% in duplex stainless steels to a range above 1% and below 4%. Reducing the nickel contents would decrease the amount of austenite present although the nitrogen and manganese contents economically offset the need for higher levels of nickel. At equivalent austenite contents, higher nickel levels act to reduce nitrogen solubility and can lead to porosity in castings. Studies on the highly alloyed super ferritic stainless alloys such as Seacure or 29-4C indicate nickel improves heavy gage toughness but promotes sigma phase and 885° F. (475° C.) embrittlement. While much of the nickel in the duplex alloy of this invention probably partitions to the austenitic phase, the nickel which remains in the 30–60% ferrite present would promote embrittlement. This propensity for the ferrite to form sigma or 885° F.(475° C.) embrittlement is reduced at the lower nickel levels of this invention. A preferred range of 2% to 3% has been found to promote the desired levels of austenite, reduce the risk of sigma phase and other embrittling phases and reduce as-cast porosity.

Nitrogen is one of the more recent changes in composition for duplex stainless steels. Nitrogen increases the strength, improves pitting resistance and forms or promotes austenite. Nitrogen has been also shown to improve general corrosion resistance in duplex alloys by reducing the tendency of chromium to partition to the ferritic phase. Nitrogen is present from 0.05% to 0.15% but must be balanced with the other elements to avoid porosity or gassiness in the steel. A preferred range is 0.07% to 0.13% and a more preferred range is 0.09% to 0.12%. Adding nitrogen to the composition allows the reduction in nickel content while still maintaining the austenitic balance. Nitrogen increases the rate of austenite formation during solidification and eliminates the need to heat treat to obtain the desired austenite ferrite balance in the as-cast condition.

Manganese levels in the steels of the invention represent the greatest departure from the traditional duplex stainless steel composition. Patents like U.S. Pat. No. 4,101,347 have taught the levels of manganese should be below 2% or sigma phase is promoted and corrosion resistance suffers. Manganese has been used previously as a deoxidizer. The solubility of the present alloy for nitrogen has now required higher manganese levels. This is particularly true for alloys having less than 22% chromium. Manganese is a strong contributor to stabilizing the austenite and is believed to be less than about one-half the strength of nickel in forming austenite. While not wishing to be bound by theory, it is believed that only the first 2% of the manganese content contributes to austenite formation. Manganese in the steels of the invention is prevent from above 4% to 8%. A preferred range is from about 4.5% to 6%. High levels of manganese have been disclosed in U.S. Pat. No. 4,657,606 but this was limited to a 25% Cr-5% Ni-2% Cu alloy with nitrogen to provide good pitting resistance and eliminate solution heat treatment. The reference is clearly directed to high chromium and high copper alloys where the % Cr plus 3X% Mo is greater than 32. Material from this patent was evaluated and found to have embrittlement problems after slow cooling from hot rolling temperature. Increasing the manganese level in these alloys did not improve resistance to embrittlement.

Silicon is present in the steels of the invention to improve castability and fluidity. Silicon is also a ferrite former and deoxidizer. In the present alloys, silicon is maintained below 2% and preferably below 1.3% since it contributes to sigma phase and other forms of embrittlement. Silicon tends to improve pitting resistance in chloride environments but is detrimental to toughness. Silicon is believed to reduce nitrogen solubility and promote nitrogen porosity and is preferably kept below 1.3%.

Molybdenum has always been required in duplex stainless steels but not in the present invention. Steels of the present invention have maintained the levels of molybdenum below 2% and typically below 1.25%. Molybdenum contributes to sigma phase and embrittlement at 885° F. (475° C.). The lowering of the molybdenum content also allows a further reduction in nickel since molybdenum is a ferrite former.

Copper is purposefully added in the present invention although levels only up to 1.5% are permitted. Typically the levels are below 1%. It permits the further economic reduction of nickel and may improve nitrogen solubility. Copper does stabilize the austenite, reduce the work hardening rate and improve the corrosion resistance to reducing acids. Copper may contribute sigma phase. With high levels of manganese, high copper levels have been found to cause hot working problems in austenitic alloys and thus should be limited to levels below 1.5%.

To improve ferrite stabilization, refine the grain structure, suppress segregation or improve intergranular corrosion, the addition up to 1% of one or more of the following optional elements singularly or in combination may be included: Niobium, tantalum, titanium, zirconium or vanadium.

Other optional elements which may be included are boron up to 0.01% to improve hot working or resistance to nitric acid. Similarly, calcium up to 0.01% may improve hot working and also resistance to stress corrosion cracking when combined with sulfur restrictions.

Sulfur normally is maintained below 0.05% but may range up to 0.35% for free machining. When added with calcium, the sulfur should be restricted to levels below 0.005%.

Phosphorus is a residual which is maintained typically below 0.05%. However, levels of phosphorus up to 0.10% may be used to improve fluidity for castings.

The balance is essentially iron and other residual elements.

Any one or more of the preferred or more preferred ranges indicated above can be used with any one or more of the broad ranges for the remaining elements set forth above.

The balance between austenite and ferrite is very important to develop the optimum combination of properties. The strength level depends strongly on the ferrite content. A minimum of 30% ferrite is required to develop a 0.2% yield strength of at least 50 ksi (350 N/mm$^2$). Good ductility requires the ferrite be maintained below 60%. The broad ferrite range is thus 30% to 60% and preferably 35% to 50% for an optimum balance in properties.

The duplex stainless steel described above has been determined to have properties ideally suited for thin-walled automotive castings. Heavywalled castings and other cast forms may be produced from this composition as well as various wrought products such as strip, sheet, plate, bar, rod and wire. Powder metal articles could also be produced from this composition. The alloy is economical, usable as-cast, has good corrosion resistance and strength and retains reasonable levels of toughness and ductility. The present alloy system has also eliminated the need for heat treatment and may be used as-cast.

The compositions, mechanical properties, and corrosion resistance of a number of steels are shown in the following tables.

TABLE I

| Heat Code | % C | % Mn | % P | % S | % Si | % Cr | % Ni | % N | % Cu | % Mo | CrE* | NiE** |
|---|---|---|---|---|---|---|---|---|---|---|---|---|
| a[1] | .034 | 4.79 | .015 | .009 | .87 | 17.76 | 1.99 | .11 | .74 | .25 | 19.3 | 6.7 |
| b[1] | .033 | 5.01 | .016 | .008 | .93 | 18.88 | 2.98 | .11 | .74 | .25 | 20.5 | 7.7 |
| c[1] | .064 | 4.97 | .016 | .009 | .92 | 19.11 | 3.03 | .11 | .74 | .25 | 20.7 | 8.5 |
| d[1] | .032 | 4.98 | .016 | .008 | .92 | 19.93 | 2.01 | .11 | .74 | .25 | 21.6 | 6.7 |
| e[1] | .032 | 4.82 | .015 | .008 | .86 | 19.87 | 3.92 | .11 | .72 | .24 | 21.4 | 8.6 |
| f[2] | .033 | 4.67 | .015 | .008 | .82 | 17.80 | 3.96 | .11 | .72 | .24 | 19.3 | 8.6 |
| g[2] | .043 | 4.07 | — | — | 1.04 | 19.22 | 1.11 | .15 | .50 | .25 | 20.8 | 6.4 |
| h[2] | .033 | 3.98 | — | — | 1.49 | 19.95 | 4.19 | .082 | .48 | .25 | 22.2 | 8.0 |
| i[2] | .030 | 3.98 | — | — | .83 | 22.58 | 2.09 | .14 | .50 | .25 | 23.8 | 6.9 |

*CrE = % Cr + 1.5 (% Si) + % Mo
**NiE = % Ni + .33 (% Mn + % Cu) + 18.4 (% N) + 24.5 (% C)
[1] steels of the invention, no porosity, toughness at 32° F. (0° C.) >20 ft.-lbs.
[2] steels outside the invention, porosity problems Table I lists the compositions for the duplex alloys tested. All compositions are given in weight %. The chromium equivalent and nickel equivalent equations are modifications of the Schaeffler Diagram which most accurately describe the amount of austenite and ferrite present.

TABLE II

| Heat Code | .2% YS (ksi) | U.T.S. (ksi) | Hardness RB | Percent Magnetism | 5% NaCl Salt Fog-Rust Coverage |
|---|---|---|---|---|---|
| a | 52.6 | 80.0 | 89.5 | 41 | 3% |
| b | 51.2 | 82.7 | 82.5 | 38 | 5% |
| c | 50.5 | 85.0 | 85.0 | 34 | 10% |
| d | 63.2 | 82.0 | 83.5 | 47 | 3% |
| e | 58.6 | 93.3 | 87.0 | 36 | 0% |
| f | 43.9 | 92.6 | 81.5 | 26 | 2% |
| g | 53.8 | 80.2 | 94 | 55 | — |
| h | 67.7 | 92.1 | 98 | 49 | — |
| i | 58.4 | 75.8 | 94.5 | 65 | — |

Table II lists the mechanical properties and corrosion data for the steels of Table I. The properties are based on air melted chemistries drawn off into a 0.2 inch (0.5 cm) inner diameter tube using a vacuum assist.

The cast 0.2 inch (0.5 cm) diameter pins were pulled as tensiles. Straight lengths were glass bead peened, pickled and exposed for 95 hours to a 5% salt fog. Red rust examinations were made visually. The rust coverage should not exceed 10% and preferably is 5% or less.

The three steels not of the invention (g, h and i) were cast as 0.6 inch (1.5 cm) diameter pins. Heat f not of the invention, was cast as a 0.2 inch (0.5 cm) pin.

Magnetism readings were determined using a Fischer scope.

Heat f illustrates the need to provide at least 30% ferrite if a minimum yield strength of 50 ksi (350 N/mm$^2$) is to be produced.

Heat g has nitrogen porosity problems due to the composition not being properly balanced. The alloy is too low in manganese for nitrogen at the upper limit of 0.15%.

Heat h also has a nitrogen porosity problem due to low manganese, and high nickel. This porosity problem occurs at a level of nitrogen far less than Heat g.

Heat i illustrates that high levels of chromium will not control nitrogen porosity when nitrogen is at the higher end of the range. The porosity problem occurs even with the nickel being about half of Heat h. Higher levels of manganese are again shown to be required for this amount of nitrogen.

The steels of the invention represent a balance of composition which produces a unique combination of properties. A cast article produced from the composition will have at least a 10% elongation in one inch (2.5 cm), a 0.2% yield strength greater than 50 ksi (350 N/mm$^2$), a toughness of at least 20 ft.-lbs. (30 Nm) at 32° F.(0° C.) and no nitrogen porosity. The duplex stainless steel must be balanced to provide 30% to 60% ferrite to obtain these properties.

What is claimed is:

1. A duplex stainless steel alloy having a microstructure of 30% to 60% ferrite, balance austenite, said alloy consisting essentially of in percentages by weight:
   less than 0.07% C,
   17% to 21.5% Cr,
   greater than 1% to less than 4% Ni,
   0.07% to 0.13% N,
   4.25% to 5.5% Mn,
   less than 2% Si,
   less than 2% Mo,
   less than 1.5% Cu and balance essentially Fe.

2. The duplex stainless steel alloy of claim 1 wherein the alloy includes up to 1% Nb, Ti, Ta, Zr and/or V.

3. The duplex stainless steel alloy of claim 1 wherein the alloy includes one or more of:
   up to 0.01% Ca,
   up to 0.10% P,
   up to 0.4% S,
   up to 0.2% Ce,
   up to 0.01% B.

4. The duplex stainless steel alloy of claim 1 wherein the carbon is less than 0.04%.

5. The duplex stainless steel alloy of claim 4 wherein the microstructure is 35–50% ferrite, balance austenite, the chromium is 18.5% to 20%, the nickel is 2% to 3%, the silicon is less than 1.3%, the molybdenum is less than 1.25% and the copper is less than 1%.

6. The duplex stainless steel alloy of claim 5 wherein the nitrogen is 0.09% to 0.12% and the sulfur is below 0.05%.

7. A duplex stainless steel article as-cast having a minimum elongation of 10% (1 inch/2.5 cm), a .2% yield strength greater than 50 ksi (350 N/mm$^2$) at 32° F.(0° C.), a microstructure of 30 to 60% ferrite, balance austenite, no nitrogen porosity, said article having a composition consisting essentially of in weight percentages:
   less than 0.07% C,
   17% to 21.5% Cr,
   greater than 1% to less than 4% Ni,
   0.07% to 0.13% N,
   4.25% to 5.5% Mn,
   less than 2% Si,
   less than 2% Mo,
   less than 1.5% Cu and
   balance essentially Fe.

8. Thin-walled duplex stainless steel article castings as claimed in claim 7.

9. Wrought duplex stainless steel article sheet, strip, plate, bar, rod and wire as claimed in claim 7.

10. Castings and powder metal articles as claimed in claim 7.

11. Duplex stainless steel article as claimed in claim 7 wherein said article has 35% to 50% ferrite, balance austenite, said article consisting essentially of in weight percent:
 less than 0.04% C,
 18.5% to 20% Cr,
 2% to 3% Ni,
 0.07% to 0.13% N,
 4.25% to 5.5% Mn,
 less than 2% Si,
 less than 1.25% Mo,
 less than 1% Cu,
 up to 0.10% P,
 balance essentially Fe.

12. Duplex stainless steel strip, sheet, plate bar, rod, wire, castings, thin-walled castings, and powder metal articles as claimed in claim 11.

13. A duplex stainless steel article as claimed in claim 11 wherein said article consists essentially, in weight percent of one or more of:
 up to 0.01% Ca,
 up to 0.10% P,
 up to 0.4% S,
 up to 0.2% Ce,
 up to 0.01% B,
 up to 1% Nb, Ti, Ta, Zr and/or V.

* * * * *